United States Patent [19]

Zengel et al.

[11] 4,404,401

[45] Sep. 13, 1983

[54] PROCESS FOR THE PREPARATION OF PARA-AMINO-DIPHENYLAMINE

[75] Inventors: Hans G. Zengel, Kleinwallstadt; Manfred Bergfeld, Erlenbach, both of Fed. Rep. of Germany

[73] Assignee: Akzona Incorporated, Asheville, N.C.

[21] Appl. No.: 14,672

[22] Filed: Feb. 23, 1979

[51] Int. Cl.³ ............................................. C07C 83/02
[52] U.S. Cl. .................................................... 564/416
[58] Field of Search ............................... 260/576, 580

[56] References Cited

U.S. PATENT DOCUMENTS

| | | | |
|---|---|---|---|
| 3,142,705 | 7/1964 | Freytag et al. | 260/576 |
| 3,927,101 | 12/1975 | Ludec | 260/580 |
| 3,978,131 | 8/1976 | Pawellek et al. | 260/576 |
| 3,992,395 | 11/1976 | Ludec | 260/580 X |
| 4,005,143 | 1/1977 | Bohm et al. | 260/580 X |

Primary Examiner—Robert V. Hines
Attorney, Agent, or Firm—Francis W. Young; Robert F. Green

[57] ABSTRACT

An improved process for the preparation of para-amino diphenylamine in which para-nitroso-diphenylhydroxylamine is catalytically hydrogenated in the presence of an organic solvent and one or more metal components selected from the group consisting of ruthenium, rhodium, palladium, osmium, iridium, and platinum, and their sulfidic compounds, at temperatures from 20° to 200° C., is disclosed. The improvement comprises utilizing as the organic solvent one or more members of the group consisting of aniline and aniline derivatives containing ring-alkyl groups, N-alkyl groups, or a combination thereof, wherein the ring-alkyl groups contain a total of 1 to 6 carbon atoms and the N-alkyl groups contain from 1 to 6 carbon atoms.

11 Claims, No Drawings

PROCESS FOR THE PREPARATION OF PARA-AMINO-DIPHENYLAMINE

BACKGROUND OF THE INVENTION

This invention relates to a process for the preparation of para-amino diphenylamine by means of the catalytic hydrogenation of para-nitroso diphenylhydroxylamine.

The hydrogenation of para-nitroso diphenylhydroxylamine to para-amino diphenylamine is well known. According to a process described in German patent application disclosure no. 1,941,008, the nitroso compound may be hydrogenated either in a liquid mixture with a hydroxylic solvent, such as water, or a primary or secondary alcohol, or in the gaseous phase. The metal catalysts used in the process are combinations of two or more of the heavy metals, iron, manganese, cobalt, copper, nickel, silver, cerium and lead, in the form of their oxides, hydroxides or carbonates. Hydrogenation may be carried out at temperatures from 100° to 250° C., preferably under elevated pressure, and is indicated to result in the desired para-amino diphenylamine, with a yield of 74 to 93%. However, the yield is not of analytically pure product, but of crude product, after removal of the solvent. Therefore, one must assume that by-products, such as products formed by hydrogenation of the nucleus, are included in the product yield.

According to the process of British Pat. No. 1,296,211, the para-nitroso diphenylhydroxylamine may be charged as its alkali derivative and hydrogenated at temperatures between room temperature and 120° C., in an aqueous medium, in the presence of a hydrogenation catalyst. Metals of Group VIII of the periodic system, for example, nickel, cobalt, ruthenium, palladium, or platinum, may be used as catalysts, which, if desired, may be applied to an inert carrier. The quantity of catalyst is from 0.1 to 10, preferably 0.1 to 2%, by weight. Hydrogenation may be carried out in the usual manner, at temperatures between room temperature and 120° C., and preferably under elevated pressure. Also, it is desirable to utilize an inert, organic solvent, which is partly or completely miscible with water, as such methanol, ethanol, n-butanol, or dioxane, or an inert, organic solvent which is not miscible with water, such as toluene, xylene or monochlorobenzene. In the process of the British patent as well, the yields of para-amino diphenylamine are in the range from 40 to 88% (crude product). According to British Pat. No. 1,304,525, when alcohols are used as solvents, good yields are obtained only in the case of propanol, isopropanol, n-butanol, and isobutanol (71 or 83% of theoretical crude product), whereas in the case of other alcohols, such as ethanol, n-amyl alcohol, and isoamyl alcohol, the yields are substantially lower (32.5, 45.8 or 41.6% of theoretical crude product).

The reduction of para-nitroso diphenylhydroxylamine to para-amino diphenylamine by means of the catalytic transfer hydrogenation is known from German patent application disclosure no. 2,715,785. Hydrogenation may be carried out in the presence of a catalyst based on a noble metal of Group VIII of the periodic system. Formic acid or a formate, a phosphorus compound with at least one hydrogen atom bonded immediately to the phosphorus, or hydrazine, which may contain up to two methyl groups, serve as hydrogen donors. The catalyst is used in quantities of up to 25% by weight, preferably up to 10% by weight of precious metal, based on the substrate. Preferably, the reduction is carried out in a mixture of water and tetrahydrofuran. The high quantity of catalyst notwithstanding, the yield of para-amino diphenylamine is only between 70 and 90%.

From the foregoing it is quite apparent that there exists a need for an improved process for the production of para-amino diphenylamine which provides for the production of such a compound in relatively high yields.

SUMMARY OF THE INVENTION

An improved process for the preparation of para-amino diphenylamine in which para-nitroso diphenylhydroxylamine is catalytically hydrogenated in the presence of an organic solvent and one or more metal components selected from the group consisting of ruthenium, rhodium, palladium, osmium, iridium, and platinum, and their sulfidic compounds, at temperatures from 20° to 200° C., is provided. The improvement comprises utilizing as the organic solvent one or more members of the group consisting of aniline, aniline derivatives having ring-alkyl groups, containing a total of 1 to 6 carbon atoms, aniline derivatives having N-alkyl groups which contain from 1 to 6 carbon atoms, and aniline derivatives having a combination of ring-alkyl and N-alkyl groups wherein the total number of ring-alkyl carbon atoms is from 1 to 6 and the N-alkyl groups contain from 1 to 6 carbon atoms.

DETAILED DESCRIPTION OF THE PREFERRED EMBODIMENTS

Para-nitroso diphenylhydroxylamine is a compound which is easily obtained by the catalytic dimerization of nitrosobenzene. According to a more recent, especially advantageous process, it is obtainable with practically quantitative yield, if a sulfonic acid with a $pK_a$ value $\leq 1$, for example, methane-, ethane-, or trifluoromethanesulfonic acid, perchloric acid, or trifluoroacetic acid are used as the catalyst, in accordance with the teachings of German patent application no. P 27 03 919. The nitrosobenzene required for the preparation of para-nitroso diphenylhydroxylamine is also easily obtainable, as through the catalytic reduction of nitrobenzene. The reduction will proceed with high yield and high selectively if, according to another recent process, an aliphatic, cycloaliphatic, olefinic, or aromatic hydrocarbon is used as the reducing agent, as taught in German patent application no. P 27 13 602.

It has now been surprisingly discovered that the amines to be used as solvents pursuant to the present invention are far superior to the customary solvents, such as water, alcohols, hydrocarbons, and acetones, with respect to the conversion, as well as the selectively. The foregoing is even more surprising, in view of the fact that it is known from the literature that aromatic nitroso compounds easily react with primary aromatic amines to form azo compounds and water, or to form diphenylamine derivatives, through condensation reactions in the para position. Furthermore, nitroso-hydroxy-aromatic compounds present in the quinoidal form can produce phenylimines (anilines) with aryl-amines, instead of azo compounds. From the literature it is also known that especially the para-nitroso diphenylhydroxylamine can easily produce a quinoidal hybrid form and, based thereon, can enter into reactions such as methylation. In this connection, reference may be made to the following literature:

W. Seidenfaden in Houben-Weyl, Methods of Organic Chemistry, 4th edition (1971), Georg Thieme Publishing House, Stuttgart, vol X/1, p. 1077; H. Feuer, The Chemistry of Nitro and Nitroso Groups, in the series The Chemistry of Functional Groups, of S. Patai, parts I and II, Interscience Publishers, New York, 1969, pp. 252 to 287; P. A. S. Smith, The Chemistry of Open Chain Nitrogen Compounds, vol. 1 and 2, W. A. Benjamin, Inc., New York—Amsterdam, 1966, pp. 361 to 368.

In the process pursuant to the invention, all metals of the platinum and palladium group, or their sulfidic compounds, may be used as catalysts. Thus, ruthenium, rhodium, palladium, osmium, iridium, and platinum, and their sulfidic compounds, are useful as catalysts in the present invention. The term "sulfidic compounds" is used to mean the commercial catalysts obtained when the referenced metals are sulfidized. Although specific, uniform metal sulfides are not involved here, such catalysts are, for the sake of simplicity, referred to in industry as palladium sulfide, platinum sulfide, and the like (cf. Robert I. Peterson, Hydrogenation Catalysts, Noyes Data Corporation, Parkridge, N.J., USA 1977, pp. 256 to 261).

Typically, the quantity of catalysts utilized in the process of the present invention is from about 0.0005 to about 1.0%, by weight, of metal, and preferably from about 0.001 to about 0.5%, by weight, of metal. Most preferably the quantity of catalyst is from about 0.005 to about 0.02%, by weight, of metal, all based on the charged para-nitroso diphenylhydroxylamine. Thereby, the endowment of the metal on the carrier, in particular on the activated carbon, may be from about 15 to about 0.1%, by weight, preferably from about 5 to about 1%, by weight.

The solvents used in the process of the present invention are aniline, or amines of a benzene homologue with 7 to 12 carbon atoms, or their mixtures. The latter amines are aniline derivatives carrying one or several alkyl groups in the benzene ring (ring-alkyl groups), with the total number of carbon atoms in the alkyl groups amounting to from 1 to about 6. Examples of such compounds are the aniline homologues ortho-, meta-, and para-toluidine; ortho-, meta-, and para-xylidine; 2,4,6-trimethyl aniline (mesidine); 2,3,5-trimethyl aniline (pseudocumidine); n-propyl aniline; orthopropyl aniline; para-isopropyl aniline (cumidine); para-tertiary butyl aniline, 2-isopropyl-5-methyl aniline (thymyl amine), 5-isopropyl-2-methyl aniline (carvacryl amine) and 2,3,4,5-tetramethyl aniline. Suitable solvents are also the N-monoalkyl and N-dialkyl derivatives of aniline and the above-mentioned aniline homologues, with the N-alkyl groups possessing 1 to 6 carbon atoms in each case. This may involve monomethyl, monoethyl, monopropyl, monobutyl, monopentyl, monohexyl, dimethyl, diethyl and dipropyl derivatives, or compounds with mixed alkyl groups. Examples of such compounds are dimethyl, diethyl and dipropyl aniline, as well as the corresponding N-substituted toluidines and xylidines. Some of the mentioned aromatic amines are solid substances under the conditions of the process pursuant to the invention and are therefore only used in mixture with other amines, that are liquid between 20° and 60° C. Preference is given to those aniline homologues and N-substituted derivatives of aniline and its homologues, whose melting and/or boiling points are sufficiently far below the melting and boiling point of para-amino diphenylamine (66°–67° C., or 354° C. in $H_2$), so that a simple separation by means of distillation and/or crystallization is possible. For economic reasons, aniline, ortho-toluidine and meta-toluidine are preferred as solvents.

The quantity of solvent is not critical. High conversion rates and selectivities during hydrogenation can also be obtained in a heterogeneous phase. The quantity of solvent should be proportioned in such a way, that the suspension can be stirred well. Furthermore, in order to achieve an economically favorable separation of the catalyst from the formed para-amino diphenylamine, it makes sense to select the concentration of para-nitrosodiphenylhydroxylamine in such a way, that at the end of the reaction the formed para-amino diphenylamine is completely dissolved. A concentration of 10 to 25% by weight of para-amino diphenylamine in the solvent has thus been found to be favorable. A greater excess of solvent is of course not harmful but, because of the dilution effect, is economically unfavorable.

The reaction pressure and temperature are also not critical. The process of the present invention may be performed at normal pressure and room temperature. However, because of the influence of pressure and temperature on the reaction rate, it is desirable to operate at elevated pressure and elevated temperature. It is thus preferable to work in a temperature range from about 20° to about 150° C., most preferably from about 30° to about 125° C. It is possible to exceed such an upper temperature limitation, but in general, such an elevated temperature does not bring any advantages, as the reaction proceeds exothermically and, because of the necessity of removing larger quantities of heat, difficulties may then occur which can only be overcome with greater technological expenditures. Additionally, there is then a greater danger that the reaction will become uncontrollable. As far as the hydrogen pressure is concerned, it is possible to work within a wide range, beginning with 1 bar, up to about 150 bar, preferably in the range from about 5 to about 30 bar, most preferably from about 7 to about 15 bar.

As is the case for all reactions involving mass transition, the reaction time in the present case is also pressure-dependent, and a shorter reaction time may be achieved with increasing hydrogen pressure. Generally, however, higher hydrogen pressure results in difficulties with the equipment and higher investments are thus required, so that the resulting advantages again are minimal.

It is not absolutely necessary to use pure hydrogen, and carrier gases, such as nitrogen, may also be utilized. It is also possible to use gas mixtures which, in addition to hydrogen, also contain carbon monoxide, for example, water gas and generator gas. In such instances, the carbon monoxide also participates in the reduction, but enough hydrogen must be present so that a complete reduction is assured.

A general statement regarding the reaction time is difficult to make as it depends upon a number of factors, such as the kind of quantity of the selected solvent and catalyst, the hydrogen pressure, the reaction temperature and the stirring velocity. Typically, however, the reaction time is from about 15 to about 45 minutes. Termination of the reaction may be determined by known means, such as by the cessation of hydrogen uptake. In the present case, determination of the fact that the para-nitroso diphenylhydroxylamine has been completely transferred can be accomplished by subjecting a sample to thin-layer chromatography. The process pursuant to the invention may be carried out continuously, as well as discontinuously.

Generally, the process may be carried out as follows: In a reaction vessel chosen in keeping with the size of the batch, para-nitroso diphenylhydroxylamine and the catalyst are suspended in an appropriate quantity of the selected solvent. After exhausting, the air is displaced by venting with nitrogen and thorough mixing, as by stirring, is provided under the selected hydrogen pressure. The reaction mixture is subsequently heated until suitable self-heating occurs, due to the exothermic reaction. Then, the reaction temperature is maintained by cooling and after the heat of reaction drops, the reaction is allowed to continue briefly at an elevated temperature. Typically, the catalyst is used wetted down with water, in order to exclude catalysis of the detonating gas reaction by the catalyst during charging and filling of the equipment with hydrogen. It is also advisable to use para-nitroso diphenylhydroxylamine wetted down with water. The quantities of water introduced in this matter do as little harm as the forming water reaction. Thus, it is unimportant whether one phase is present in the course in the reaction, or a second, aqueous phase forms as a result of the forming water of reaction. After termination of the reaction (as a rule with quantitative conversion), the reaction mixture is processed in the usual manner. First, the contents of the reactor are cooled, the reaction vessel pressure removed, and the catalyst filtered off at temperatures between about 20° and about 60° C. The formed water of reaction can then be separated in the usual manner, but it can also be removed together with the solvent, when the reaction products are separated, if necessary by distillation.

The process pursuant to the invention makes possible the catalytic hydrogenation of para-nitroso diphenylhydroxylamine to para-amino diphenylamine in an advantageous manner, by which it is particularly possible to work with very small quantities of precious metal catalysts. It was not expected that solely by the selection of the solvents to be used pursuant to the present invention, it would be possible to obtain higher conversion rates and selectivities, than with the customary solvents, such as toluene, methanol, isopropanol, and acetone. Furthermore, the process pursuant to the present invention is distinguished by its relatively short reaction time of about 15 to about 45 minutes, whereas in the known processes, even after a reaction time of 6 hours, and in the most favorable prior art case, less than 90% of the theoretical yield of para-amino diphenylamine is obtained.

The para-amino diphenylamine obtainable pursuant to the present invention is an intermediate product in the manufacture of dyestuffs, and is in particular required in the manufacture of asymmetrical phenylene diamine derivatives, which are used as antidecredants in rubber mixtures.

EXAMPLES 1 TO 5

The reactions are carried out in a 1 liter glass autoclave, equipped with a bottom outlet valve, a gas supply tube, a flow breaker, a vaned stirrer, and a manometer. The reaction is carried out between about 40° and about 150° C. with hydrogen pressure between about 5 and about 30 bar, for a reaction time of about 30 minutes, and with a stirring velocity of 1500 rpm. First, the autoclave is evacuated, then vented with hydrogen, and subsequently, half the solvent is added. The para-nitroso diphenylhydroxylamine, together with the catalyst, is suspended in the second half of the reaction medium and added through an inlet valve by means of hydrogen pressure. After that, the autoclave is put under hydrogen pressure and heated carefully. Depending upon the other reaction parameters, the reaction begins between about 20° and about 70° C. Additional heat is applied after the heat of reaction drops, so that the total reaction time is 30 minutes. Subsequently, the pressure is removed from the autoclave and the catalyst filtered off at a somewhat elevated temperature (about 30° to about 50° C.). If the catalyst is to be used for additional cycles, the catalyst is flushed back into the reaction space while still moist with solvent. If the catalyst is to be used only once, the still adhering solvent is washing out with a more volatile solvent, such as methanol or methylene chloride.

First the water of reaction, then the solvent, and finally the para-amino diphenylamine are obtained separately from the filtrate by means of fractional distillation. When larger quantities of para-amino diphenylamine are made, it is advisable to connect a flaker to the distillation column and in such an instance, the para-amino diphenylamine is obtained in the form of white flakes with a faintly beige cast.

The processing conditions as well as the resulting yields of para-amino diphenylamine are compiled in the following Table I. In each case, 20 grams, (93.2 mmol) of para-nitroso diphenylhydroxylamine are utilized. The following catalysts obtained from the firm Degussa are employed:

A: E1OR, palladium on carbon, palladium endowment 1% by weight.
B: E1OR, palladium on carbon, palladium endowment 5% by weight.
C: F1O3RS, platinum sulfide on carbon, platinum endowment 5% by weight.
D: E1O1RS, palladium sulfide on carbon, palladium endowment 4.88% by weight.
E: F1O1R, patinum on carbon, platinum endowment 1% by weight.

The following abbreviations are used in the Table: NDHA=para-nitroso diphenylhydroxylamine; ADA=para-amino diphenylamine; CPPD=N-cyclohexyl-para-phenylene diamine.

EXAMPLES 6 to 15

The following examples, or comparative examples, are carried out in the manner described for Examples 1 through 5. The examples show the superiority of the process pursuant to the present invention, which is considerable, especially with respect to the use of catalysts with a low metal content. As palladium catalyst, use is made of the palladium-carbon catalyst E1OR of the firm Degussa, with a 1%, by weight, palladium endowment, while the nickel catalyst was Raney nickel.

TABLE I

| Example No. | Catalyst Type | Catalyst % by Wt. Metal Ref. to NDHA | Solvent Amine | Solvent % by Wt. Ref. to NDHA | ml | % Water Ref. to NDHA | Temp. °C. | Press. Bar | Convers. % | Yield % ADA of th. | By-prod. % CPPD of th. |
|---|---|---|---|---|---|---|---|---|---|---|---|
| 1 | A | 0.5 | aniline | 1020 | 200 | — | 75 | 15 | 100 | 97.5 | 2.1 |
| 2 | B | 0.1 | o-toluidine | 724.5 | 150 | — | 100 | 10 | 100 | 98.2 | 0.8 |
| 3 | C | 0.5 | aniline | 1020 | 200 | 50 | 125 | 15 | 100 | 99.2 | — |
| 4 | D | 0.2 | aniline | 1020 | 200 | 75 | 120 | 15 | 100 | 97.5 | 0.2 |
| 5 | E | 0.5 | o-toluidine | 744.7 | 150 | — | 80 | 10 | 100 | 96.2 | 3.1 |

From the data contained in Tables I and II, it is apparent that the process of the present invention is capable of producing yields from about 91 to about 99% of the theoretical yield of para-amino diphenylamine. This in contrast to the yields obtained with the same process utilizing different solvents such as acetone, methanol, isopropanol, toluene, and ethanol, which produced yields in the range from about 30 to about 80% of the theoretical yield of para-amino diphenylamine.

TABLE II

| Example No. | Catalyst Type | Catalyst % by Wt. Metal Ref. to NDHA | Solvent Type | ml | % Water Ref. to NDHA | % Water Ref. to NDHA | Temp. °C. | Press. Bar | Convers. % | ADA % of th. |
|---|---|---|---|---|---|---|---|---|---|---|
| 6* | Pd/C | 0.01 | acetone | 150 | 592 | 100 | 75 | 10 | 80 | 30 |
| 7* | Pd/C | 0.01 | methanol | 200 | 790 | — | 100 | 10 | 30 | 26.5 |
| 8* | Pd/C | 0.01 | methanol | 200 | 790 | 200 | 100 | 10 | 65 | 55 |
| 9* | Pd/C | 0.01 | isopropanol | 200 | 785 | 20 | 125 | 15 | 50 | 15 |
| 10* | Pd/C | 0.01 | toluene | 200 | 871.5 | — | 100 | 10 | 20 | 15 |
| 11* | Ni | 10 | acetone | 120 | 474 | — | 50–150 | 50 | 45 | 24.5 |
| 12* | Ni | 10 | ethanol | 150 | 592 | — | 85 | 50 | 30 | 20.5 |
| 13 | Pd/C | 0.01 | aniline | 200 | 1020 | — | 100 | 10 | 100 | 94.6 |
| 14 | Pd/C | 0.01 | aniline | 200 | 1020 | 100 | 100 | 10 | 95 | 92.5 |
| 15 | Pd/C | 0.01 | o-toluidine | 150 | 724.5 | — | 100 | 10 | 95 | 91 |

*Denotes Comparative Example

What we claim is:

1. In an improved process for the preparation of para-amino diphenylamine in which para-nitroso-diphenylhydroxylamine is catalytically hydrogenated in the presence of an organic solvent and one or more metal compounds selected from the group consisting of ruthenium, rhodium, palladium, osmium, iridium, and platinum, and their sulfidic compounds, at temperatures from about 20° to 200° C., the improvement comprising utilizing as the organic solvent one or more members of the group consisting of aniline and aniline derivatives containing ring-alkyl groups, N-alkyl groups, and combinations thereof, wherein the ring-alkyl groups contain a total of 1 to 6 carbon atoms and the N-alkyl groups each contain from 1 to 6 carbon atoms.

2. The process of claim 1 wherein the metal component is selected from the group consisting of palladium on activated carbon, platinum on activated carbon, palladium sulfide on activated carbon, and platinum sulfide on activated carbon.

3. The process of claim 1 or 2 wherein the hydrogenation is performed at a temperature from about 30° to about 125° C.

4. The process of claim 1 or 2 wherein the organic solvent is selected from the group consisting of aniline, ortho-toluidine, and meta-toluidine.

5. The process of claim 4 wherein the hydrogenation is performed at a temperature from about 30° to about 125° C.

6. The process of claim 1 or 2 wherein the hydrogenation is performed at a hydrogen pressure of from about 1 to about 30 bar.

7. The process of claim 6 wherein the hydrogenation is performed at a temperature from about 30° to about 125° C.

8. The process of claim 7 wherein the organic solvent is selected from the group consisting of aniline, ortho-toluidine, and meta-toluidine.

9. The process of claim 1 wherein the quantity of metal component is from about 0.0001 to about 0.5%, by weight of metal, based on the para-nitroso-diphenylhydroxylamine.

10. The process of claim 8 wherein the quantity of metal component is from about 0.001 to about 0.5%, by weight of metal, based on the para-nitroso-diphenylhydroxylamine.

11. The process of claim 1 wherein the organic solvent is selected from the group consisting or ortho-toluidine, meta-toluidine, para-toluidine, ortho-xylidine, meta-xylidine, para-xylidine, 2,4,6-trimethyl aniline, 2,3,5-trimethyl aniline, N-propyl aniline, ortho-propyl aniline, para-isopropyl aniline, para-tertiary butyl aniline, 2-isopropyl-5-methyl aniline, 5-isopropyl-2-methyl aniline, 2,3,4,5-tetramethyl aniline, dimethyl aniline, diethyl aniline, and dipropyl aniline.

* * * * *